US007919306B2

(12) United States Patent
Takagi

(10) Patent No.: US 7,919,306 B2
(45) Date of Patent: Apr. 5, 2011

(54) BIOLOGICAL SAMPLE REACTION CHIP, BIOLOGICAL SAMPLE REACTION APPARATUS, AND BIOLOGICAL SAMPLE REACTION METHOD

(75) Inventor: Fumio Takagi, Chino (JP)

(73) Assignee: Seiko Epson Corporation (JP)

(*) Notice: Subject to any disclaimer, the term of this patent is extended or adjusted under 35 U.S.C. 154(b) by 28 days.

(21) Appl. No.: 12/328,870

(22) Filed: Dec. 5, 2008

(65) Prior Publication Data

US 2009/0148912 A1 Jun. 11, 2009

(30) Foreign Application Priority Data

Dec. 6, 2007 (JP) ................................ 2007-316322

(51) Int. Cl.
*C12M 1/34* (2006.01)

(52) U.S. Cl. ..................... 435/288.5; 435/293.1; 422/72

(58) Field of Classification Search ............... 435/288.5, 435/293.1; 422/72
See application file for complete search history.

(56) References Cited

U.S. PATENT DOCUMENTS 4,284,602 A * 8/1981 Kelton et al. ................... 422/72
5,518,930 A * 5/1996 Burd ............................... 436/45
5,589,350 A * 12/1996 Bochner ......................... 435/29
6,990,290 B2 1/2006 Kylberg et al.
7,582,259 B2 * 9/2009 Ogawa et al. ................... 422/72
7,691,328 B2 * 4/2010 Horiike et al. .................. 422/72
2006/0245972 A1 11/2006 Osone et al.

FOREIGN PATENT DOCUMENTS

JP 2000-236876 9/2000
JP 2004-513779 5/2004
JP 2006-126010 5/2006
JP 2006-126011 5/2006
JP 2006-308366 11/2006
JP 2007-304053 11/2007
JP 2008-122151 5/2008
JP 2008-122152 5/2008

OTHER PUBLICATIONS

Yoshihiro Nagaoka, "Flows in Chip for Use in Centrifugal Analysis", "Flows 21", (2002), pp. 419-428.

* cited by examiner

*Primary Examiner* — William H Beisner
(74) *Attorney, Agent, or Firm* — Harness, Dickey & Pierce, P.L.C.

(57) ABSTRACT

A biological sample reaction chip, including: a plurality of reactors disposed on one plane; a reaction fluid distribution channel connected via a microchannel to each reactor and provided on the plane on which the plurality of reactors are disposed; and a reaction fluid movement stopping unit, which is connected to an end point of the reaction fluid distribution channel and is capable of controlling movement of a reaction fluid.

11 Claims, 4 Drawing Sheets

BIOLOGICAL SAMPLE REACTION CHIP, BIOLOGICAL SAMPLE REACTION APPARATUS, AND BIOLOGICAL SAMPLE REACTION METHOD

CROSS-REFERENCES TO RELATED APPLICATIONS

This application relates to and claims priority from Japanese Patent Application No. 2007-316322, filed on Dec. 6, 2007, the entire disclosure of which is incorporated herein by reference.

BACKGROUND

1. Technical Field

The present invention relates to a biological sample reaction chip, a biological sample reaction apparatus and a biological sample reaction method, which are intended for the purpose of carrying out biological sample reactions such as nucleic acid amplification.

2. Related Art

Methods for carrying out chemical analysis, chemical synthesis or bio-related analysis using microfluidic chips in which microchannels are provided on a glass substrate or the like have been attracting attention. Microfluidic chips, also known as μ-TAS (micro-Total Analytical System) or Lab-on-a-chip, provide a number of advantages over devices of the related art. For example, the sample and reagent amounts required are small, the reaction time is short, and the amount of waste generated is small. Such advantages offer promise for the use of these devices in a broad range of fields, including medical diagnostics, on-site environmental and food analysis, and the manufacture of pharmaceuticals and chemical products. Because the amount of reagent used is small, the cost of tests can be lowered. Moreover, the small amounts of sample and reagent used enable the reaction time to be considerably shortened, resulting in greater test efficiency. When such devices are used for medical diagnosis in particular, the smaller size of specimens such as blood collected for use as the sample has the added advantage of being less onerous to the patient.

The polymerase chain reaction (PCR) is familiar as a method of amplifying genes such as DNA or RNA used as reagents or samples. The PCR method is carried out by placing a mixture of the target DNA and reagent in a tube and, within a temperature control device known as a thermal cycler, effecting a reaction by repeatedly varying the temperature between three levels, that is, 55° C., 72° C. and 94° C. in cycles of several minutes each. It is possible in this way, through the action of the enzyme known as polymerase, to amplify only the target DNA about two-fold per temperature cycle.

In recent years, a process known as real-time PCR which employs a special fluorescent probe has come into practical use, making it possible for the DNA to be quantitatively determined as the reaction is being carried out. Real-time PCR is widely used in research and clinical tests on account of its sensitivity of measurement and high reliability.

However, in an apparatus of the related art, the amount of reaction fluid required for the PCR is typically several tens of microliters, and it is basically possible to measure only one gene in a single reaction system. Although there does exist a method in which a plurality of fluorescent probes are inserted and, by distinguishing between the colors thereof, about four types of genes are simultaneously measured, the only way to measure more genes than this at the same time has been to increase the number of reaction systems. Because the amount of DNA extracted from a specimen is generally small and the reagents are expensive, carrying out measurement simultaneously in a large number of reaction systems has been difficult.

JP-A-2006-126010 and JP-A-2006-126011 disclose inventions in which, using a rotationally driven apparatus, PCR reaction solutions and samples of liquid specimens such as blood are accurately delivered to a plurality of chambers.

JP-A-2000-236876 discloses a method in which an array of microwells is created on a semiconductor substrate and PCR reactions are carried out within the wells, thereby using very small sample quantities to amplify a large number of DNA samples at the same time and carry out analysis.

SUMMARY

It is therefore an object of the invention to provide a biological sample reaction chip, a biological sample reaction apparatus and a biological sample reaction method, so as to enable reaction fluids in very small quantities of one microliter or less to be supplied to reactors by a simple method and make it possible to efficiently carry out the treatment of numerous specimens at one time.

The biological sample reaction chip according to one aspect of the present invention has a plurality of reactors disposed on one plane; a reaction fluid distribution channel connected via a microchannel to each reactor and provided on the plane on which the plurality of reactors are disposed; and a reaction fluid movement stopping unit, which is connected to an end point of the reaction fluid distribution channel and is capable of controlling movement of a reaction fluid.

The present invention makes it possible to supply to the reactors in predetermined amounts even very small quantities of a reaction fluid suitable for filling the reactors by applying to the biological sample reaction chip a centrifugal force oriented from the starting point to the end point of a reaction fluid distribution channel, yet difficult to quantitatively deliver with a pipette. It is possible in this way to supply to reactors by a simple method a reaction fluid available in a scarce amount, and to efficiently carry out reaction treatment. Moreover, because a small amount of the reaction fluid suffices, costs can be lowered. In addition, the reaction time is considerably shortened, resulting in more efficient treatment. Also, treatment can be carried out in many reactors at the same time, enabling a plurality of different tests, for example, to be efficiently carried out with small amounts of reagents.

It is desirable that the biological sample reaction chip also have a reaction fluid reservoir connected to a starting point of the reaction fluid distribution channel. This arrangement makes it possible, by supplying the reaction fluid reservoir beforehand with reaction fluid and applying a centrifugal force, to introduce the reaction fluid into the reaction fluid distribution channel, thus enabling the reactors to be filled with the reaction fluid by a simple mechanism using centrifugal force.

It is desirable for the biological sample reaction chip to also have a waste fluid reservoir connected to the reaction fluid movement stopping unit. This arrangement makes it possible to efficiently recover, using centrifugal force, reaction fluid that has not been supplied to the reactors.

In addition, a reagent necessary for reaction may be coated onto each reactor. This enables the user to easily carry out tests or the like by merely filling the reactors with the reaction fluid.

The biological sample reaction apparatus according to another aspect of the invention is an apparatus for carrying out biological sample reaction treatment using the above-described biological sample reaction chip, and includes both a fixture for fixing the biological sample reaction chip about a center of rotation, and a centrifuge for spinning the biological sample reaction chip so that a centrifugal force acts thereon in a direction oriented from the starting point to the end point of the reaction fluid distribution channel.

This arrangement makes it possible for even very small quantities of reaction fluids to be supplied in predetermined amounts to the interior of the reactors. It is possible in this way to supply to the reactors by a simple method a reaction fluid available in a limited amount, and efficiently carry out reaction treatment. Moreover, because a small amount of the reaction fluid suffices, costs can be lowered. In addition, the reaction time is greatly shortened, resulting in more efficient treatment. Also, because treatment can be carried out in numerous reactors at the same time, a plurality of different tests, for example, may be efficiently carried out using a small amount of reagent.

In the biological sample reaction chip of the foregoing biological sample reaction apparatus, the reaction fluid movement stopping unit may be a U-shaped channel which is connected at one end thereof to the end point of the reaction fluid distribution channel and which has thereon a top located at a shorter distance from the center of rotation than the reaction fluid distribution channel.

This arrangement makes it possible to obtain a reaction fluid movement stopping unit suitable for filling the reactors with the reaction fluid by a simple mechanism using centrifugal force. Moreover, at the time that a centrifugal force is being applied to the biological sample reaction chip, it is necessary for the position at the leading end of the reaction fluid when movement of the reaction fluid stops owing to an equilibrium between the capillary force incurred by the reaction fluid advancing through the interior of the U-shaped channel and the centrifugal force to be short of the top of the U-shaped channel. This makes it possible to prevent the reaction fluid from flowing out of the reaction fluid distribution channel.

It is desirable for the waste fluid reservoir to be connected to the other end of the U-shaped channel at a junction therebetween, and the junction is located at a greater distance from the center of rotation than the end point of the reaction fluid distribution channel.

In this arrangement, when the biological sample reaction chip is spun after the U-shaped channel has become filled with the reaction fluid by capillary action, because the waste fluid reservoir is located at a position farther from the center of rotation than the end point of the reaction fluid distribution channel, the reaction fluid present within the reaction fluid distribution channel can be completely discharged by a siphoning effect.

The biological sample reaction method according to yet another aspect of the invention uses the above-described biological sample reaction apparatus and includes the steps of: supplying the reaction fluid to the biological sample reaction chip; spinning the biological sample reaction chip so as to apply a centrifugal force oriented from the starting point to the end point of the reaction fluid distribution channel and thereby fill each reactor with the reaction fluid; and carrying out biological sample reaction treatment. Movement of the reaction fluid is stopped by the reaction fluid movement stopping unit in the step of filling each reactor with the reaction fluid.

This method enables even very small quantities of a reaction fluid to be supplied in predetermined amounts to the interior of the reactors. It is possible in this way to supply to reactors by a simple method a reaction fluid available in a scarce amount, and to efficiently carry out reaction treatment. Moreover, because a small amount of the reaction fluid suffices, costs can be lowered. In addition, the reaction time is considerably shortened, resulting in more efficient treatment. Also, treatment can be carried out in a plurality of reactors at the same time, enabling a plurality of different tests, for example, to be efficiently carried out with small amounts of reagents.

It is preferable for the biological sample reaction method of the invention to include, between the step of filling each reactor with the reaction fluid and the step of carrying out biological sample reaction treatment, the steps of: spinning the biological sample reaction chip so as to apply a centrifugal force oriented from the starting point to the end point of the reaction fluid distribution channel and thereby discharge the reaction fluid from within the reaction fluid distribution channel; and filling the reaction fluid distribution channel with a liquid which is non-miscible with the reaction fluid and evaporates less readily than the reaction fluid.

This method, by filling the reaction fluid distribution channel with a liquid which is non-miscible with the reaction fluid and evaporates less readily than the reaction fluid, isolates the individual reactors, enabling contamination between the reactors to be prevented. Moreover, evaporation of the reaction fluid during reaction treatment can be prevented.

A biological sample reaction method according to a still further aspect of the invention uses a U-shaped channel as the reaction fluid movement stopping unit in the above-described biological sample reaction chip and includes the steps of: supplying the reaction fluid to the biological sample reaction chip; spinning the biological sample reaction chip so as to apply a centrifugal force oriented from the starting point to the end point of the reaction fluid distribution channel and thereby fill each reactor with the reaction fluid; stopping rotation so that the reaction fluid advances within the U-shaped channel under a capillary force and reaches the waste fluid reservoir; spinning the biological sample reaction chip so as to apply a centrifugal force oriented from the starting point to the end point of the reaction fluid distribution channel and thereby discharge the reaction fluid from within the reaction fluid distribution channel; filling the reaction fluid distribution channel with a liquid which is non-miscible with the reaction fluid and evaporates less readily than the reaction fluid; and carrying out biological sample reaction treatment. In the step of filling each reactor with the reaction fluid, the capillary force in the U-shaped channel and the centrifugal force are placed in equilibrium, thereby stopping movement of the reaction fluid before the top of the U-shaped channel.

This arrangement makes it possible to obtain a reaction fluid movement stopping unit suitable for filling the reactors with the reaction fluid by a simple mechanism using centrifugal force. Moreover, in the step of filling each reactor with the reaction fluid, because the capillary force in the U-shaped channel and the centrifugal force are placed in equilibrium, movement of the reaction fluid is stopped before the top of the U-shaped channel, making it possible to prevent the reaction fluid from flowing out from within the reaction fluid distribution channel.

In the foregoing biological sample reaction methods according to the invention, the biological sample reaction treatment may include nucleic acid amplification, the reaction fluid may contain a target nucleic acid, an enzyme for amplifying nucleic acid and a nucleotide, and the reactors may be coated beforehand with a primer.

Also, when real-time PCR treatment is carried out, the interior of the reactors may be coated beforehand with a fluorescent probe.

The reaction fluid movement stopping unit is not limited to a U-shaped channel, and may be selected from among any of various units which function as a valve on the chip. For example, if the channel is formed of a material such as polydimethylsiloxane (PDMS) which readily deforms under an external force, the channel can be mechanically closed. Alternatively, a method which involves, for example, the use of a porous filter, narrowing of the channel width, or water-repelling treatment of the channel inside walls may instead be selected. In cases such as the latter that involve using the surface tension of a liquid, the movement and stopping of the reaction fluid can be controlled by the rotational speed of the centrifuge.

DESCRIPTION OF EXEMPLARY EMBODIMENTS

A preferred embodiment of the invention is described below in conjunction with the appended diagrams.

First Embodiment

Figure 1A:
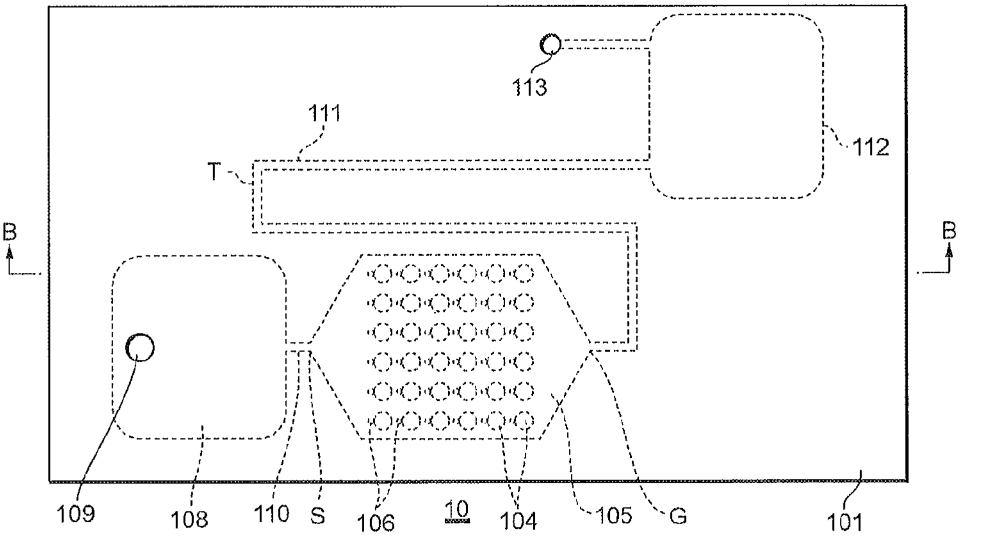
FIG. 1A is a top view schematically showing a microreactor array according to a first embodiment of the present invention.
Figure 1B:
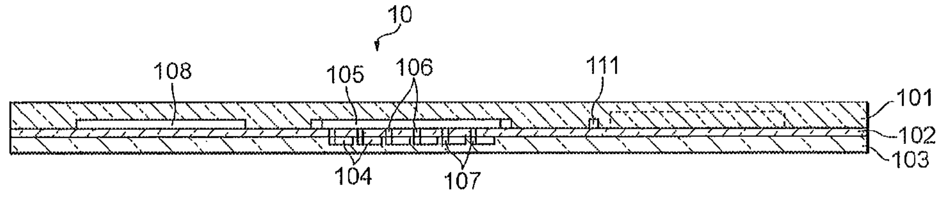
FIG. 1B is a cross-sectional view taken along B-B in FIG. 1A.

FIG. 1A is a top view schematically showing a microreactor array (biological sample reaction chip) 10 according to a first embodiment of the present invention, and FIG. 1B is a cross-sectional view taken along B-B in FIG. 1A. As shown in the diagrams, the microreactor array 10 has transparent substrates 101, 102 and 103, reactors 104, a reaction fluid distribution channel 105, throughholes 106, microchannels 107, a reaction fluid reservoir 108, a reaction fluid feed port 109, a connecting channel 110 connecting the reaction fluid reservoir 108 with the reaction fluid distribution channel 105, a U-shaped channel (reaction fluid movement stopping unit) 111, a waste fluid reservoir 112, and an exhaust port 113 provided in the waste fluid reservoir 112.

As shown in FIG. 1, the microreactor array 10 is constructed of a first transparent substrate 101, a second transparent substrate 102 and a third transparent substrate 103 which are laminated together. The first transparent substrate 101 has formed therein a reaction fluid distribution channel 105, a reaction fluid reservoir 108, a reaction fluid feed port 109, a connecting channel 110, a U-shaped channel 111, a waste fluid reservoir 112 and an exhaust port 113. The second transparent substrate 102 has throughholes 106 formed therein. The third transparent substrate 103 has a plurality of reactors 104 and a plurality of microchannels 107 formed therein. The transparent substrates 101, 102 and 103 may be glass substrates, in which case the above-mentioned structural features in each may be formed by etching or sandblasting.

The microchannels 107, the connecting channel 110 and the U-shaped channel 111 are formed so that the respective cross-sections perpendicular to the direction of flow by the reaction fluid have a width of 200 μm and a depth of 100 μm. The reaction fluid distribution channel 105 and the throughholes 106 are each formed to a depth of 100 μm.

Figure 2A:
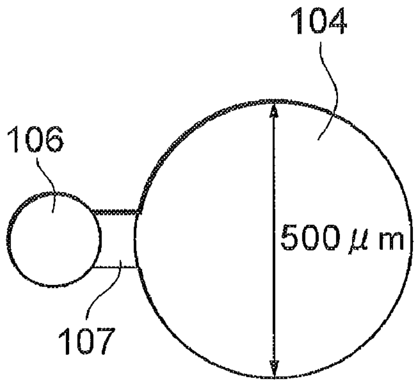
FIG. 2A is a top view of a reactor.
Figure 2B:
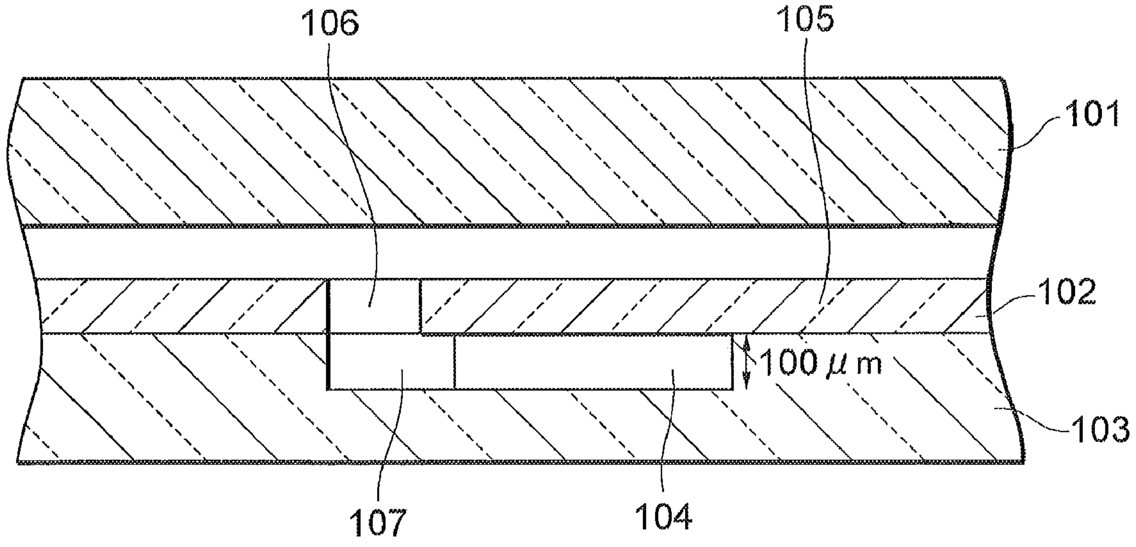
FIG. 2B is a cross-sectional view of the same.

FIG. 2 shows the construction of a reactor 104, FIG. 2A being a top view of the reactor and FIG. 2B being a cross-sectional view of the same. The reactor 104 is formed, for example, in a circular shape having a diameter of 500 μm and to a depth of 100 μm. The reactor 104 communicates with the reaction fluid distribution channel 105 via the throughhole 106 and the microchannel 107. Mutually adjoining reactors 104 are kept a sufficient distance apart to prevent the mixing of reaction fluids between the reactors 104.

It is desirable to surface treat the inside walls of the reactors 104 and the inside walls of the reaction fluid distribution channel 105 to make them hydrophilic and thereby prevent the adsorption of bubbles. Alternatively, it is desirable for the inside walls of the reactors 104 and the inside walls of the reaction fluid distribution channel 105 to be surface-treated to suppress the nonspecific adsorption of biomolecules such as protein.

A method for supplying the reaction fluid to the microreactor array 10 is described while referring to FIG. 3. The reaction fluid includes a target nucleic acid, a polymerase and a nucleotide (dNTP) in specific concentrations suitable for reaction.

The target nucleic acid may be, for example, DNA extracted from biological samples such as blood, urine, saliva or cerebrospinal fluid, or cDNA reverse-transcripted from extracted RNA.

A primer may be present in the reaction fluid. However, in the microreactor array 10 of the present embodiment, the interior of each reactor 104 has been pre-coated with primer and held in a dry state. Each reactor 104 has been coated with a different primer so as to make it possible to carry out a plurality of PCRs at the same time.

Figure 3A:
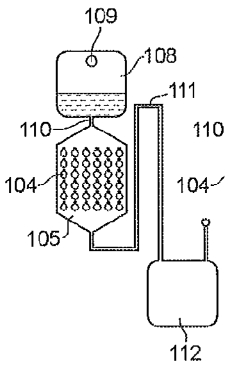
FIG. 3A, FIG. 3B, FIG. 3C, FIG. 3D, FIG. 3E, and FIG. 3F are views illustrating a method of supplying reaction fluid to a microreactor array according to the first embodiment of the invention.

First, as shown in FIG. 3A, using a pipette or the like, reaction fluid is supplied to the reaction fluid reservoir 108 from the reaction fluid feed port 109. At this time, the reaction fluid stops at the junction between the connecting channel 110 and the reaction fluid distribution channel 105, and does not enter into the reaction fluid distribution channel 105. This is because the capillary force P1 at the junction between the connecting channel 110 and the reaction fluid distribution channel 105 is larger than the capillary force P2 in the reaction fluid distribution channel 105.

Generally, when a liquid advances into a very small channel, a capillary force P expressed by the following formula acts on the liquid.

$$P=(L\gamma\cos\theta)/S$$

Here, L is the circumferential length of the channel cross-section perpendicular to flow, S is the surface area thereof, $\gamma$ is the surface tension, and $\theta$ is the contact angle. Letting the values $\gamma$ and $\theta$ in the respective channels be constant, the size of the capillary force for each channel is determined by the value of the ratio L/S.

Figure 4:
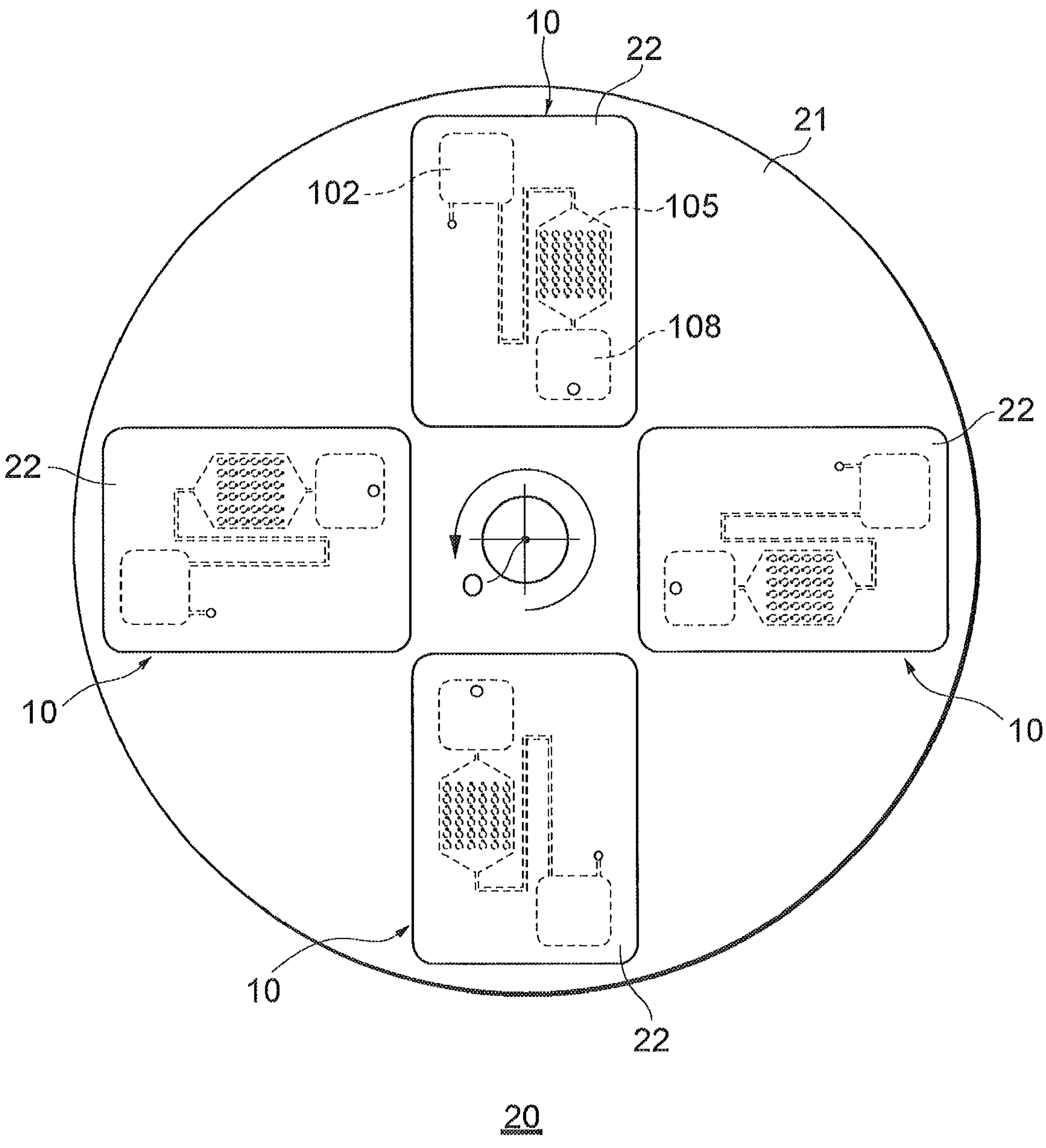
FIG. 4 is a schematic diagram showing a centrifuge according to the first embodiment of the invention.

Next, the microreactor array 10 is spun using the centrifuge (biological sample reaction apparatus) 20 shown in FIG. 4.

Referring to FIG. 4, the centrifuge 20 is composed of a turntable 21 on which fixtures 22 for the placement of microreactor arrays 10 are arranged about an axis of rotation O. Spinning the centrifuge 20 causes a centrifugal force to be applied to the microreactor arrays 10 in a direction oriented from the starting point S to the end point G of the reaction fluid distribution channel 105.

Figure 3B:
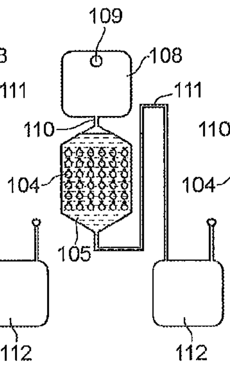

As shown in FIG. 3B, the application of a centrifugal force to the microreactor array 10 causes the reaction fluid to advance while filling the reaction fluid distribution channel 105, and to additionally pass through the throughholes 106 and the microchannels 107, filling the reactors 104. Because the reactors 104 are formed at positions farther from the center of rotation than the throughholes 106 and the microchannels 107, air which has a lower specific gravity than the reaction fluid is pushed through the microchannels 107 and the throughholes 106, and into the reaction fluid distribution channel 105, where it displaces the reaction fluid, as a result of which the reactors 104 become filled with the reaction fluid.

When the reaction fluid reaches the end point G of the reaction fluid distribution channel 105, it advances into the U-shaped channel 111 by capillary force. However, because centrifugal force is being applied to the microreactor array 10, the reaction fluid advancing through the U-shaped channel 111 stops at a position where the capillary force and the centrifugal force are in equilibrium. That is, the reaction fluid stops at a position where the distance between the front of the meniscus within the U-shaped channel 111 and the center of rotation is the same as the distance between the front of the meniscus within the reaction fluid distribution channel 105 and the center of rotation. Because the U-shaped channel 111 acts in this way as a reaction fluid movement stopping unit, the reaction fluid does not flow toward the waste fluid reservoir 112 and can instead be made to enter and fill the reactors 104.

To ensure that the front of the meniscus within the U-shaped channel 111 is positioned before the top T of the U-shaped channel 111, it is necessary to not exceed the upper limit in the amount of reaction fluid. If the reaction fluid passes through the top T of the U-shaped channel 111, the reaction fluid will readily advance along the U-shaped channel 111 in the direction away from the center of rotation, as a result of which the U-shaped channel 111 will become filled with the reaction fluid, which will flow into the waste fluid reservoir 112 by a siphoning effect. On the other hand, if the amount of the reaction fluid is below the lower limit, it may be impossible to fill all of the reactors 104.

Figure 3C:
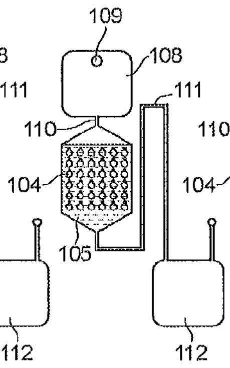

Next, when rotation is stopped, as shown in FIG. 3C, the reaction fluid advances through the U-shaped channel 111 by capillary force. However, because the capillary force P3 of the U-shaped channel 111 is larger than the capillary force P4 of the waste fluid reservoir 112, the reaction fluid stops when it reaches the inlet to the waste fluid reservoir 112.

Figure 3D:
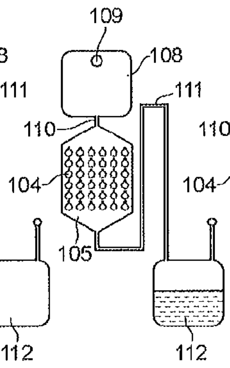

When the microreactor array 10 is spun once again by the centrifuge 20, because the waste fluid reservoir 112 is farther from the center of rotation than the reaction fluid distribution channel 105 and the U-shaped channel 111, as shown in FIG. 3D, due to the centrifugal force and a siphoning effect, the reaction fluid within the reaction fluid distribution channel 105 and the U-shaped channel 111 flows into and is held by the waste fluid reservoir 112. At this time, the reaction fluid held in the reactors 104 is not discharged from the reactors 104.

Figure 3E:
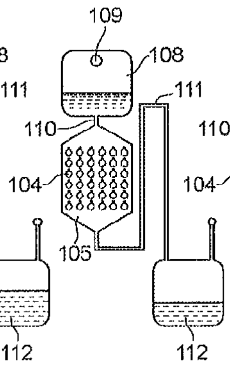

Next, rotation is stopped and, as shown in FIG. 3E, mineral oil is supplied from the reaction fluid feed port 109 to the reaction fluid reservoir 108 using a pipette or the like.

Figure 3F:
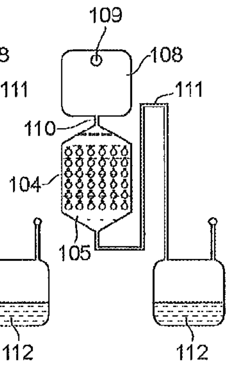

By then additionally spinning the microreactor array 10 on the centrifuge 20, as shown in FIG. 3F, the mineral oil fills the reaction fluid distribution channel 105. Because the reaction fluid has a higher specific gravity than the mineral oil, the reaction fluid within the reactors 104 is not dislodged by the mineral oil at this time. It is possible in this way to isolate the individual reactors 104 and prevent contamination between the reactors 104. This also enables drying within the reactors 104 to be prevented during reaction treatment. Instead of mineral oil, a liquid which has a lower specific gravity than the reaction fluid, is non-miscible with the reaction fluid, and evaporates less readily than the reaction fluid may be used.

Once the reaction fluid has been fed to the microreactor array 10 by a procedure like that described above, the microreactor array 10 is placed in a thermal cycler and PCR treatment is carried out. Generally, a cycle which includes the steps of, first, dissociating double-stranded DNA at 94° C., then annealing the primer at about 55° C., and finally replicating the complementary strand at about 72° C. using heat-resistant DNA polymerase, is repeatedly carried out.

Next, a method for carrying out real-time PCR using the microreactor array 10 is described.

When a microreactor array 10 is used as the reaction apparatus for a real-time PCR reaction, the primer and fluorescent probe used in the PCR reaction are pre-coated onto the inside walls of the reactors 104, and the fluorescent intensity for each cycle is measured using, for example, a charge-coupled device (CCD) sensor. The initial amount of the target nucleic acid is calculated and measured from the number of cycles required to reach a specific fluorescent intensity. It should be noted that the method of carrying out real-time PCR is not limited to that described above. For example, in cases where a double-stranded DNA binding fluorescent dye such as SYBR (registered trademark) Green is used, a fluorescent probe is not necessary.

As described above, according to the first embodiment, because the reaction fluid is filled into the reactors 104 by applying to the microreactor array 10 a centrifugal force oriented from the starting point S to the end point G of the reaction fluid distribution channel 105, even when the amount of reaction fluid available for use is very small, the reactors 104 can be filled with predetermined amounts of the reaction fluid. When the amount of reaction fluid is smaller, its thermal capacity is lower, making it possible to shorten the PCR cycle time, shorten the reaction time, and thus achieve greater treatment efficiency. Because treatment can be carried out in numerous reactors 104 at the same time, it is possible to efficiently carry out a plurality of different tests or the like using small amounts of reagent. Moreover, by coating the respective reactors 104 with the primers and fluorescent probes required for amplification and quantitative determination of the target nucleic acids, the user can easily carry out PCR treatment by merely filling the reactors 104 with the reaction fluid.

In the present embodiment, the reaction fluid is introduced via a connecting channel 110 to the reaction fluid distribution channel 105 by providing a reaction fluid reservoir 108 and spinning the microreactor array 10, although it is possible to supply the reaction fluid directly to the reaction fluid distribution channel 105 without providing a reaction fluid reservoir 108. However, in such a case, a means must be provided to control the reaction fluid and keep it from passing through the end point G of the reaction fluid distribution channel 105 before centrifugal force is applied to the microreactor array 10. The reason is that, if the reaction fluid enters the U-shaped channel 111 before centrifugal force is applied, the U-shaped channel 111 will become filled with the reaction fluid due to capillary forces, and the reaction fluid will flow out into the waste fluid reservoir 112 due to a siphoning effect.

In the first embodiment, the microreactor array 10 is used as the reaction apparatus for real-time PCR reaction, and may be employed in various reactions using genes and biological samples. For example, the microreactor array 10 may be used in treatment which involves coating the reactors 104 with antigens that specifically complement (e.g., adsorb, bind) specific proteins or with antibodies, receptors, proteins such as enzymes, or peptides (oligopeptides), and detecting the target protein from the reaction fluid.

What is claimed is:

1. A biological sample reaction chip, comprising:

a plurality of reactors disposed on one plane in a matrix;

a reaction fluid distribution channel provided on a plane above the plane on which the plurality of reactors are disposed, the reaction fluid distribution channel including a starting point, an end point, and an intermediate part between the starting point and the end point, the intermediate part being connected via a microchannel to each reactor; and a reaction fluid movement stopping unit connected to the end point of the reaction fluid distribution channel, the reaction fluid movement stopping unit being adapted to control movement of a reaction fluid, when the biological sample reaction chip is rotated about a rotational axis to exert a centrifugal force from the starting point toward the end point of the reaction fluid distribution channel, each of the reactors being located farther from the rotational axis than the microchannels.

2. The biological sample reaction chip according to claim 1, further comprising a reaction fluid reservoir connected to the starting point of the reaction fluid distribution channel.

3. The biological sample reaction chip according to claim 1, further comprising a waste fluid reservoir connected to the reaction fluid movement stopping unit.

4. The biological sample reaction chip according to claim 1, a reagent necessary for reaction being coated onto each reactor.

5. A biological sample reaction apparatus for carrying out biological sample reaction treatment using the biological sample reaction chip of claim 1, the apparatus comprising:

a fixture for fixing the biological sample reaction chip about the rotational axis; and a centrifuge for spinning the biological sample reaction chip so that the centrifugal force acts thereon in a direction oriented from the starting point to the end point of the reaction fluid distribution channel.

6. The biological sample reaction apparatus according to claim 5, wherein the reaction fluid movement stopping unit in the biological sample reaction chip is a U-shaped channel, which is connected at one end thereof to the end point of the reaction fluid distribution channel and which has thereon a top located at a shorter distance from the rotational axis than the starting point of the reaction fluid distribution channel.

7. The biological sample reaction apparatus according to claim 6, the waste fluid reservoir being connected to the other end of the U-shaped channel at a junction therebetween, and the junction is located at a greater distance from the rotational axis than the end point of the reaction fluid distribution channel.

8. A biological sample reaction method using the biological sample reaction apparatus of claim 6, comprising the steps of:

supplying the reaction fluid to the biological sample reaction chip;

spinning the biological sample reaction chip so as to apply the centrifugal force oriented from the starting point to the end point of the reaction fluid distribution channel and thereby fill each reactor with the reaction fluid;

stopping rotation so that the reaction fluid advances within the U-shaped channel under a capillary force and reaches the waste fluid reservoir;

spinning the biological sample reaction chip so as to apply the centrifugal force oriented from the starting point to the end point of the reaction fluid distribution channel and thereby discharge the reaction fluid from within the reaction fluid distribution channel;

filling the reaction fluid distribution channel with a liquid which is non-miscible with the reaction fluid and evaporates less readily than the reaction fluid; and carrying out biological sample reaction treatment, wherein, in the step of filling each reactor with the reaction fluid, the capillary force in the U-shaped channel and the centrifugal force are placed in equilibrium, thereby stopping movement of the reaction fluid before the top in the U-shaped channel.

9. A biological sample reaction method using the biological sample reaction apparatus of claim 5, comprising the steps of:

supplying the reaction fluid to the biological sample reaction chip;

spinning the biological sample reaction chip so as to apply the centrifugal force oriented from the starting point to the end point of the reaction fluid distribution channel and thereby fill each reactor with the reaction fluid; and carrying out biological sample reaction treatment, movement of the reaction fluid being stopped by the reaction fluid movement stopping unit in the step of filling each reactor with the reaction fluid.

10. The biological sample reaction method according to claim 9, further comprising, between the step of filling each reactor with the reaction fluid and the step of carrying out biological sample reaction treatment, the steps of:

spinning the biological sample reaction chip so as to apply the centrifugal force oriented from the starting point to the end point of the reaction fluid distribution channel and thereby discharge the reaction fluid from within the reaction fluid distribution channel; and filling the reaction fluid distribution channel with a liquid which is non-miscible with the reaction fluid and evaporates less readily than the reaction fluid.

11. The biological sample reaction method according to claim 9, wherein the biological sample reaction treatment includes nucleic acid amplification, the reaction fluid contains a target nucleic acid, an enzyme for amplifying nucleic acid and a nucleotide, and the reactors are coated beforehand with a primer.

* * * * *